United States Patent [19]
Abra et al.

[11] Patent Number: 6,126,966
[45] Date of Patent: *Oct. 3, 2000

[54] LIPOSOMES CONTAINING A CISPLATIN COMPOUND

[75] Inventors: Robert M. Abra, San Francisco; Karen Reis, San Jose, both of Calif.

[73] Assignee: Sequus Pharmaceuticals, Inc., Menlo Park, Calif.

[*] Notice: This patent is subject to a terminal disclaimer.

[21] Appl. No.: 09/342,741

[22] Filed: Jun. 29, 1999

Related U.S. Application Data

[63] Continuation of application No. 08/915,345, Aug. 22, 1997, Pat. No. 5,945,122.
[60] Provisional application No. 60/024,350, Aug. 23, 1996.

[51] Int. Cl.[7] .................................................. A61K 9/127
[52] U.S. Cl. .......................................................... 424/450
[58] Field of Search .............................. 424/450; 264/4.1, 264/4.3

[56] References Cited

U.S. PATENT DOCUMENTS

| 5,178,876 | 1/1993 | Khokhar et al. . | |
| 5,252,336 | 10/1993 | Iga | 424/450 |
| 5,945,122 | 8/1999 | Abra | 424/450 |

FOREIGN PATENT DOCUMENTS

91/05546  5/1991  WIPO .

OTHER PUBLICATIONS

Chen, B.W. et al., "Fluorescence Study on The Interaction Between Cisplatin and Erythrocyte Membrane Proteins," *Journal of Chinese Pharmaceutical Sciences*. 4: (03) (1995).
Freise, W.H. et al., "Pharmacokinetics of Liposome Encapsulated Cisplatin in Rats," *Arch. Int. Pharmacodyn.* 258: 180–192 (1982).
Gondal, J.A. et al., "Comparative Pharmacological, Toxicological and Antitumoral Evaluation of Free and Liposome–Encapsulated Cisplatin in Rodents," *Eur J Cancer*. 29A:(11) 1536–1542 (1993).
Iga, K. et al., "Membrane Modification by Negatively Charged Stearyl–Polyoxyethylene Derivatives for Thermosensitive Liposomes: Reduced Liposomal Aggregation and Avoidance of Reticuloendothelial System Uptake," *Journal of Drug Targeting*. 2: 259–267 (1994).
Kaledin, V.I. et al., "Intralymphatic Administration of Liposome–Encapsulated Drugs to Mice: Possibility for Suppression of the Growth of Tumor Metastases in the Lymph Nodes," *JNCI*. 66:(05) 881–887 (1981).
Li, C. et al., "Formation and Characterization of Cisplatin–Loaded Poly(benzyll–glutamate) Microspheres for Chemoembolization," *Pharmaceutical Research*. 11:(12) 1792–1799 (1994).
Lu, J.F. et al., "A Study of Interaction of Cisplatin and Its Analogues with Phospholipid of Erythrocyte Membrane," *Journal of Chinese Pharmaceutical Sciences*. 4:(03) 136–143 (1995).
Potkul, R.K. et al., "Toxicities in Rats with Free Versus Liposomal Encapsulated Cisplatin," *Am J Obstet Gynecol*. 164:(02) 652–658 (1991).
Prestayko, A.W., "Cisplatin and Anologues: A New Class of Anticancer Drugs," *Cancer and Chemo*. 3 Crooke, Stanley (Ed) and Prestayko, Archie (Ed), Academic Press NY, pp. 133–154 (1981).

(List continued on next page.)

*Primary Examiner*—Gollamudi S. Kishore
*Attorney, Agent, or Firm*—Judy M. Mohr; Iota Pi Law Group

[57] ABSTRACT

A liposome composition containing an entrapped cisplatin compound is described. The liposomes have a surface coating of hydrophilic polymer chains on inner and outer surfaces and an entrapped cisplatin compound. The compound is entrapped with substantially greater retention in the liposomes, when compared to liposomes lacking the polymer coating. A method of preparing the composition is also described.

14 Claims, 6 Drawing Sheets

OTHER PUBLICATIONS

Steerenberg, P.A. et al., "Liposomes as a Drug Carrier System for cis–Diamminedichloroplatinum (II). I. Binding Capacity, Stability and Tumor Cell Growth Inhibition In Vitro," *International Journal of Pharmaceutics*. 40: 51–62 (1987).

Steerenberg, P.A. et al., "Liposomes as Drug Carrier System for cis–Diamminedichloroplatinum (II)," *Cancer Chemother. Pharmacol*. 21: 299–307 (1988).

Sur, B. et al., "Effect of Liposomal Encapsulation of cis–Platinum Diamminodichloride in the Treatment of Ehrlich Ascites Carcinoma," *Oncology*. 40: 372–376 (1983).

Taylor, K.D. et al., "Pressure Tuning Infrared Spectroscopic Study of Cisplatin–Induced Structural Changes in a Phosphatidylserine Model Membrane," *British Journal of Cancer*. 72: 1400–1405 (1995).

Weiss, R.B. and Christian, M.C., "New Cisplatin Analogue in Development," *Drugs*. 46:(03) 360–377 (1993).

Yatvin, M.B. et al., "Selective Delivery of Liposome–Associated cis–Dichlorodiammineplatinum(II) by Heat and Its Influence on Tumor Drug Uptake and Growth," *Cancer Research*. 41: 1602–1607 (1981).

LIPOSOMES CONTAINING A CISPLATIN COMPOUND

This application claims the priority of U.S. patent application Ser. No. 08/915,345 filed Aug. 22, 1997, now U.S. Pat. No. 5,945,122, which claims priority of U.S. Provisional Application Ser. No. 60/024,350, filed Aug. 23, 1996, which are incorporated herein by reference.

FIELD OF THE INVENTION

The present invention relates to a liposomal composition containing an entrapped cisplatin compound.

REFERENCES

Freise, J., et al., Arch. Int. Pharmacodyn. 258:180–192 (1982).
Gondal, J. A., et al., Eur. J. Cancer 29A(11):1536–1542 (1993).
Mabrey, S., et al., Biochem. 17:2464–2468 (1978).
Martin, F. J., in SPECIALIZED DRUG DELIVERY SYSTEMS-MANUFACTURING AND PRODUCTION TECHNOLOGY, (P. Tyle, Ed.) Marcel Dekker, New York, pp. 267–316 (1990).
PHYSICIAN'S DESK REFERENCE, 48TH EDITION, Medical Economics Data Production Co., Montvale, N.J. (1994).
Potkul, R. K., et al., Am. J. Obstet Gynecol. 164(2): 652–658 (1991).
Prestayko, A. W., CANCER AND CHEMO. VOL III (Crooke, et al., Eds.) Academic Press, NY, 133–154 (1981).
Steerenberg, P. A., et al, International Journal of Pharmaceutics 40:51–62 (1987).
Sur, B., et al, Oncology 40:372–376 (1983).
Szoka, F., Jr., et al., Ann. Rev. Biophys. Bioeng. 9:467 (1980).
Tsong, T. Y., Biochem. 14:5409–5414, 5415–5417 (1975).
Weiss, R. B., et al., Drugs 46(3):360–377 (1993).

BACKGROUND OF THE INVENTION

Cisplatin—cis-diamine-dichloroplatinum (II)—is one of the more effective anti-tumor agents used in the systemic treatment of germ cell cancers. This chemotherapeutic drug is highly effective in the treatment of tumor models in laboratory animals and in human tumors, such as endometrial, bladder, ovarian and testicular neoplasms, as well as squamous cell carcinoma of the head and neck (Sur, et al., 1983; Steerenberg, et al., 1987).

Like other cancer chemotherapeutic agents, cisplatin is a highly toxic drug. The main disadvantages of cisplatin are its extreme nephrotoxicity, which is the main dose-limiting factor, its rapid excretion via the kidneys, with a circulation half life of only a few minutes, and its strong affinity to plasma proteins (Freise, et al., 1982).

Attempts to minimize the toxicity of the drug have included combination chemotherapy, synthesis of cisplatin analogues (Prestayko, 1991; Weiss, et al., 1993), immunotherapy and entrapment in liposomes (Sur, et al., 1983; Weiss, et al., 1993). Antineoplastic agents, including cisplatin, entrapped in liposomes have a reduced toxicity, relative to the agent in free form, while retaining antitumor activity (Steerenberg, et al., 1987; Weiss, et al., 1993).

Cisplatin, however, is difficult to efficiently entrap in liposomes because of the drug's low aqueous solubility, approximately 1.0 mg/ml at room temperature, and low lipophilicity, both of which contribute to a low drug/lipid ratio.

Liposomes containing cisplatin suffer from another problem—stability of the composition. In particular, maintenance of drug potency and retention of the drug in the liposome during storage are recognized problems (Freise, et al., 1982; Gondal, et al., 1993; Potkul, et al., 1991; Steerenberg, et al., 1987; Weiss, et al., 1993) and a limited shelf life of liposomes containing cisplatin, on the order of several weeks at 4° C., has been reported (Gondal, et al., 1993; Potkul, et al., 1991).

SUMMARY OF THE INVENTION

In one aspect, the invention includes a liposomal composition containing an entrapped cisplatin compound. The composition includes liposomes having an outer surface and an inner surface defining an aqueous liposome compartment. The liposomes are composed of a vesicle-forming lipid and between about 1–20 mole percent of a vesicle-forming lipid derivatized with a hydrophilic polymer. The liposomes are formed such that the hydrophilic polymer forms a coating of hydrophilic polymer chains on both the inner and outer surfaces. The cisplatin compound is entrapped in the liposomes with substantially greater retention than in liposomes lacking the inner and outer polymer surface coatings.

The cisplatin compound, in one embodiment, is native cisplatin and is entrapped in the liposomes at a drug-to-lipid ratio of between about 10 to 20 $\mu$g/mg total lipid. In another embodiment, the cisplatin compound is a cisplatin analogue.

In another embodiment, the hydrophilic polymer chains are composed of a hydrophilic polymer selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide. In a preferred embodiment, the hydrophilic polymer is polyethyleneglycol.

The liposomes, in one embodiment have sizes between about 80–160 nm, preferably 100–140 nm, most preferably between about 100–120 nm.

In a preferred embodiment, the vesicle forming lipid is hydrogenated soy phosphatidylcholine and the derivatized vesicle forming lipid is distearyl phosphatidylethanolamine derivatized with polyethylene glycol.

In another aspect, the invention includes a method of entrapping a cisplatin compound in liposomes, by heating an aqueous solution of a cisplatin compound to a temperature sufficient to increase its solubility over the compound's solubility at room temperature. To the heated cisplatin compound solution is added a vesicle-forming lipid and between about 1–20 mole percent of a vesicle-forming lipid derivatized with a hydrophilic polymer. By said adding, liposomes having an inner surface coating and an outer surface coating of hydrophilic polymer chains are formed and the cisplatin compound is entrapped in the liposomes with substantially greater retention than in liposomes lacking the polymer coatings.

In one embodiment of the method, the cisplatin compound is native cisplatin and the aqueous cisplatin solution is heated to a temperature sufficient to achieve a two-fold to eight-fold increase in cisplatin solubility over its room temperature solubility.

In another embodiment, a solution of vesicle-forming lipids heated to within about 10° C. of the temperature of the cisplatin solution is added to the cisplatin compound solution.

In another embodiment, added to the cisplatin solution is a solution containing a vesicle-forming lipid having a phase transition temperature within about 10° C. of the temperature to which the cisplatin solution is heated.

In another embodiment, the vesicle-forming lipid solution added to the cisplatin solution contains a vesicle-forming lipid having a phase transition temperature between 40–70° C.

These and other objects and features of the invention will be more fully appreciated when the following detailed description of the invention is read in conjunction with the accompanying drawings.

DETAILED DESCRIPTION OF THE INVENTION

I. Liposome Composition

The liposomal composition of the present invention includes liposomes having a stably entrapped cisplatin compound. As used herein, "stably entrapped cisplatin compound" refers to native cisplatin or a cisplatin analogue captured within a liposome, primarily within the aqueous space of the liposome, such that the cisplatin compound is retained substantially within the liposome prior to administration.

Figure 1:
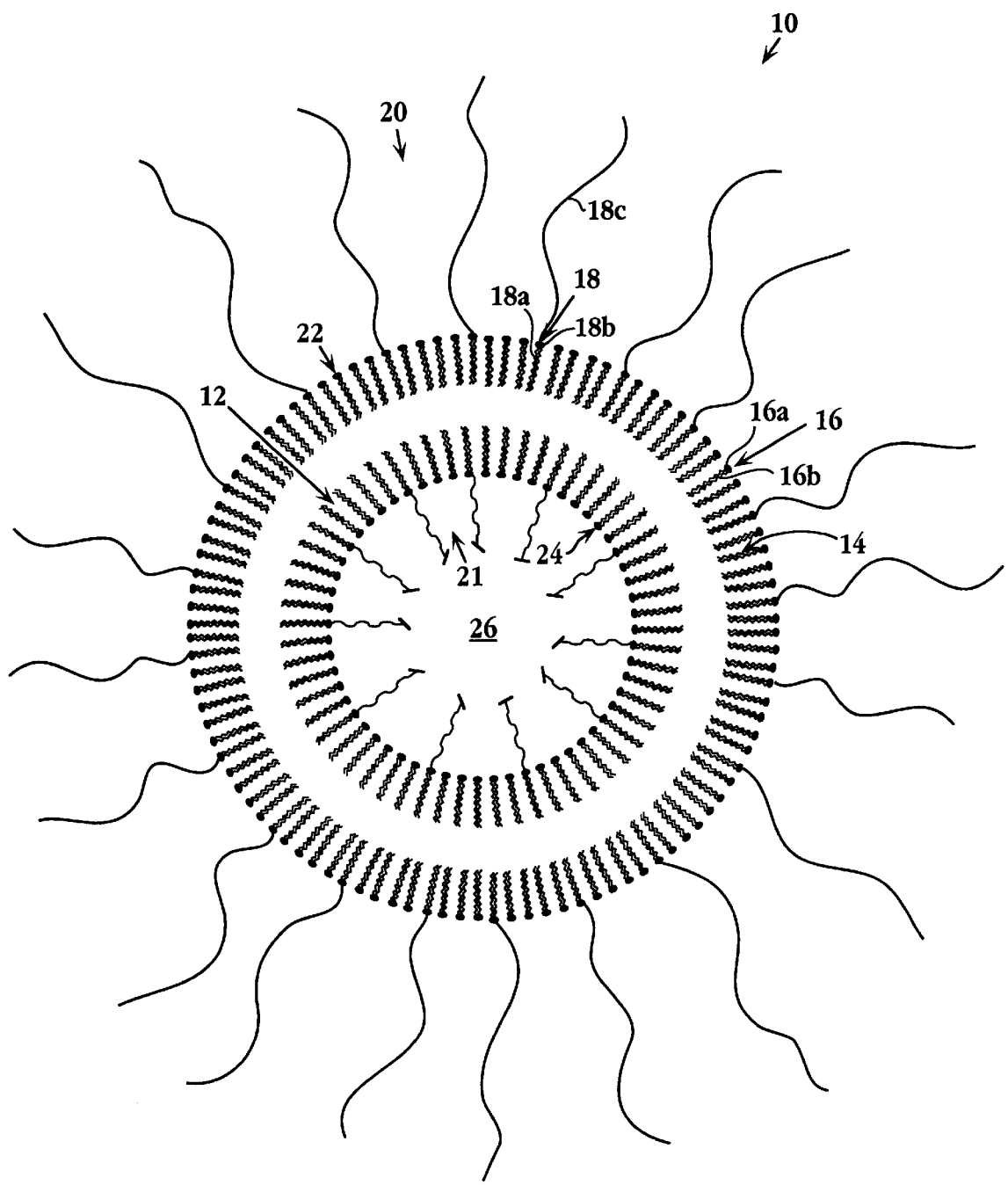
FIG. 1 is a schematic illustration of a liposome formed in accordance with the present invention.

FIG. 1 illustrates a liposome 10, prepared in accordance with the invention, which includes an inner lipid bilayer 12 and an outer lipid bilayer 14. The inner and outer lipid bilayers are formed predominantly of vesicle-forming lipids, such as lipid 16, which include a polar head group 16a and a hydrophobic tail 16b. Exemplary vesicle-forming lipids are listed below.

Liposome 10 also includes vesicle-forming lipids derivatized with a hydrophilic polymer, such as derivatized lipid 18 in FIG. 1. Derivatized lipid 18 includes a hydrophobic tail 18a, a polar head group 18b, and attached to the polar head group, by means described below, a hydrophilic polymer 18c. The hydrophilic polymer provides surface coatings 20, 21 of hydrophilic polymer chains on both an outer surface 22 of outer lipid bilayer 14 and an inner surface 24 of inner lipid bilayer 12. The outer surface coating of hydrophilic polymer chains is effective to provide a liposome with a long blood circulation lifetime in vivo. As will be illustrated below, the inner and outer surface coatings are further effective in providing a cisplatin liposomes composition with a long shelf life, e.g., a stable liposome composition where the cisplatin compound is retained in the liposome.

Liposome 10 also includes a cisplatin compound, e.g., native cisplatin or a cisplatin analogue, in entrapped form. The drug is entrapped in the inner aqueous compartment 26 in dissolved form or in precipitated form. In studies performed in support of the invention, native cisplatin was entrapped in liposomes prepared with a surface coating of hydrophilic polymer chains on the liposome's inner and outer surfaces. These liposomes, when compared to liposomes lacking the hydrophilic polymer coating, had an improved stability, as evidenced by the ability to retain the drug in its native state within the liposome for a longer period of time.

A. Vesicle-Forming Lipid Component

The liposome composition of the present invention is composed primarily of vesicle-forming lipids. Such a vesicle-forming lipid is one which (a) can form spontaneously into bilayer vesicles in water, as exemplified by the phospholipids, or (b) is stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids of this type are preferably ones having two hydrocarbon chains, typically acyl chains, and a polar head group. There are a variety of synthetic vesicle-forming lipids and naturally-occurring vesicle-forming lipids, including the phospholipids, such as phosphatidylcholine (PC), phosphatidylethanolamine (PE), phosphatidic acid (PA), phosphatidylinositol (PI), and sphingomyelin (SM), where the two hydrocarbon chains are typically between about 14–22 carbon atoms in length, and have varying degrees of unsaturation. A preferred lipid for use in the present invention is hydrogenated soy phosphatidylcholine (HSPC).

The above-described lipids and phospholipids whose acyl chains have varying degrees of saturation can be obtained commercially or prepared according to published methods.

The vesicle-forming lipid may be selected to achieve a specified degree of fluidity or rigidity, to control the stability of the liposome in serum and to control the rate of release of the entrapped agent in the liposome. Liposomes having a more rigid lipid bilayer, or a liquid crystalline bilayer, are achieved by incorporation of a relatively rigid lipid, e.g., a lipid having a relatively high phase transition temperature, e.g., up to 80° C. Rigid, i.e., saturated, lipids contribute to greater membrane rigidity in the lipid bilayer. Other lipid components, such as cholesterol, are also known to contribute to membrane rigidity in lipid bilayer structures.

Lipid fluidity is achieved by incorporation of a relatively fluid lipid, typically one having a lipid phase with a relatively low liquid to liquid-crystalline phase transition temperature, e.g., at or below room temperature (20–25° C.).

Lipids suitable for use in the cisplatin liposome composition of the present invention include vesicle-forming lipids having phase transition temperatures at or below room temperature and those having a high phase transition temperature. In a preferred embodiment, a vesicle-forming lipid having a phase transition temperature between about 40–70° C. is employed. In another embodiment, the lipid used in forming the liposomes is one having a phase transition temperature within about 20° C., more preferably 10° C., most preferably 5° C., of the temperature to which the solution containing the cisplatin compound is heated during liposome preparation, as will be described. Phase transition temperatures of lipids are tabulated in a variety of sources, such as Avanti Polar Lipids catalogue and Lipid Thermotropic Phase Transition Database (LIPIDAT, NIST Standard Reference Database 34).

The liposomes may include other lipids that can stabilize a vesicle or liposome composed predominantly of phospholipids. A frequently employed lipid for this purpose is cholesterol at between 25 to 40 mole percent. At between 0 to 20 mole percent cholesterol in a bilayer, separate domains exist containing cholesterol and phospholipids and pure phospholipid (Mabrey, et al., 1978). These bilayers show an increased permeability to water (Tsong, 1975). In one embodiment of the present invention, cholesterol is included in the liposome composition, as will be described below.

In the method of the invention, liposomes containing a cisplatin compound are prepared by adding to a heated aqueous solution of a cisplatin compound a mixture of vesicle-forming lipids containing between 1–20 mole percent of a vesicle-forming lipid derivatized with a hydrophilic polymer. The lipids are dissolved in a suitable lipid solvent, such as ethanol, methanol, chloroform or mixtures thereof.

Prior to adding the lipids, the aqueous solution of cisplatin compound is heated to a temperature sufficient to increase its solubility over the room temperature solubility of the cisplatin compound. That is, the solution is heated to a temperature that achieves at least about a two-fold, preferably a four-fold, most preferably an eight-fold, increase in solubility over the aqueous room temperature solubility of the cisplatin compound. For example, cisplatin, having an aqueous solubility of 1 mg/ml at 20–25° C. may be heated to about 63° C. to increase the aqueous solubility to about 8.5 mg/ml. The solubility of cisplatin and of cisplatin analogues can be readily determined by one of skill in the art according to standard procedures.

In one embodiment of the invention, the solution containing the vesicle-forming lipid is heated to within about 20° C., more preferably 10° C., most preferably 5° C., of the temperature of the cisplatin solution.

In the example detailed below, the vesicle-forming lipid HSPC, the derivatized vesicle-forming lipid PEG-DSPE and cholesterol are dissolved in ethanol heated to about 65° C., just above HSPC phase transition temperature's between about 52–60° C. An aqueous solution of native cisplatin is heated to between 63–67° C. The solutions are mixed together to form liposomes containing the cisplatin compound in entrapped form. The method of the invention achieves a high encapsulation of cisplatin, typically encapsulating between 10–20 μg drug/mg lipid, and provides liposomes having, in addition to the outer surface coating, an inner surface coating of hydrophilic polymer chains, with the cisplatin compound stably entrapped within the liposome.

B. Derivatized Vesicle-forming Lipid Component

As discussed above, the liposomes of the present invention have a surface coating of hydrophilic polymer chains on both the inner and outer lipid bilayer surfaces. The surface coating is provided by including in the liposome composition between about 1–20 mole percent of a lipid derivatized with a hydrophilic polymer.

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide. The polymers may be employed as homopolymers or as block or random copolymers.

A preferred hydrophilic polymer chain is polyethyleneglycol (PEG), preferably as a PEG chain having a molecular weight between 500–10,000 daltons, more preferably between 1,000–5,000 daltons. Methoxy or ethoxy-capped analogues of PEG are also preferred hydrophilic polymers, commercially available in a variety of polymer sizes, e.g., 120–20,000 daltons.

Vesicle-forming lipids suitable for derivatization with a hydrophilic polymer include any of those lipids listed above, and, in particular phospholipids, such as distearyl phosphatidylethanolamine (DSPE). Preparation of DSPE derivatized with PEG is described below (Example 1).

The derivatized lipid is incorporated into the liposome by including an amphipathic lipid derivatized with hydrophilic polymer with vesicle-forming lipids during formation of the lipid vesicles.

Once a liposome has been formed, the hydrophilic polymer chains provide a surface coating of chains on both the inner and outer surfaces of the lipid bilayer, as discussed with respect to FIG. 1. Importantly, the surface coating is effective to improve the stability of the liposomes, as will be described below. The surface coating is also effective to extend the blood circulation time of the liposomes in the absence of such a coating. The extent of enhancement of blood circulation time is preferably severalfold over that achieved in the absence of the polymer coating, as described in co-owned U.S. Pat. No. 5,013,556.

C. Other Liposome Components

The liposomes in the composition of the present invention may include other components, such as targeting molecules, including antibodies, antibody fragments, or cell-surface recognition molecules, which are attached to the liposome by means of a hydrophilic polymer chains. For example, a vesicle-forming lipid is derivatized with a hydrophilic polymer chain, as described above, and the hydrophilic polymer is end-functionalized for coupling antibodies to its functionalized end. The functionalized end group may be a hydrazide or hydrazine group which is reactive toward aldehyde groups, although any of a number of PEG-terminal reactive groups for coupling to antibodies may be used. Hydrazides can also be acylated by active esters or carbodiimide-activated carboxyl groups. Acyl azide groups reactive as acylating species can be easily obtained from hydrazides and permit attachment of amino-containing molecules. The functionalized end group may also be 2-pyridyldithio-propionamide, for coupling an antibody or other molecule to the liposome through a disulfide linkage.

D. Cisplatin Compound

The liposome composition of the present invention is intended for use in cancer therapy, more particularly in tumor therapy. A cisplatin compound is entrapped within the liposomes and the liposome composition is administered to the subject. As referred to herein, cisplatin compound refers to native cisplatin and its analogues. In a preferred embodiment, the cisplatin compound is native cisplatin and in another embodiment, the cisplatin compound is a cisplatin analogue, preferably a hydrophilic cisplatin analogue.

Native cisplatin, also referred to herein as cisplatin, is a heavy metal complex containing a central atom of platinum surrounded by two chloride atoms and two ammonia molecules in the cis position. It is a yellow powder with the molecular formula $PtCl_2H_6N_2$, and a molecular weight of 300.1. It is soluble at room temperature in water or saline at 1 mg/ml and has a melting point of 207° C. (PHYSICIAN's DESK REFERENCE, 1994) and decomposes at 270° C.

The chlorine atoms in the cisplatin molecule are subject to chemical displacement reactions by nucleophiles, such as water or sulfhydryl groups. In aqueous media, water molecules are potential ligands, which may replace the chlorine atoms to form monohydroxymonochloro cis-diamine platinum (II).

The drug is available as a sterile aqueous solution containing 1 mg cisplatin and 9 mg NaCl per ml water and in this form is typically administered intravenously for tumor therapy at a dose of between about 20–120 mg/m$^2$ (PHYSICIAN'S DESK REFERENCE, 1994). The drug may be administered alone or in combination with other chemotherapeutic agents, as a bolus injection or as a slow infusion over a period of several hours.

As a single agent, cisplatin can be administered, for example, at a dose of 100 mg/m$^2$ intravenously once every 4 weeks (PHYSICIAN'S DESK REFERENCE, 1994) or at a dose of 20 mg/m$^2$ cisplatin given as a rapid intravenous infusion daily for 5 days and repeated at 4-week intervals (Prestayko, 1991). In treatment of squamous cell cancer of the head and neck, cisplatin given intravenously as a 24-hour infusion at a dose of 80 mg/m$^2$ achieved favorable response (Prestayko, 1991).

While active as a single agent, cisplatin is often administered in combination with other agents, including vinblastine, bleomycin, actinomycin, adriamycin, prednisone, vincristine, and others (Prestayko, 1991). For example, therapy of ovarian cancer may include 60 mg/m$^2$ cisplatin and 60 mg/m$^2$ adriamycin administered as a 24-hour infusion. In the present invention, combination therapy may include liposome-entrapped cisplatin administered with another chemotherapeutic agent in free form or in liposome-entrapped form, such as liposome-entrapped doxorubicin described in U.S. Pat. No. 5,527,528.

In the present invention, cisplatin is entrapped in the liposomes which are sized to between about 80–160 nm, more preferably between about 100–140 nm, most preferably between about 100–120 nm, suitable for intravenous administration. The cisplatin-containing liposomes are administered at the dosages given above for the free drug, however, such dosages may be adjusted accordingly to account for the reduced toxicity of the drug provided by liposomal entrapment. Such an adjusted dosage can be readily determined experimentally by one of skill in the art.

The internal liposomal concentration of cisplatin is between 1–9 mg cisplatin/ml, more preferably between 4–9 mg/ml, most preferably between 6–8.5 mg/ml. The cisplatin-containing liposome suspension is at a concentration of between about 1–2 mg cisplatin/ml total suspension volume, for intravenous administration.

In another embodiment of the invention, the cisplatin compound entrapped within the liposomes is a cisplatin analogue. A wide spectrum of cisplatin analogues have been synthesized, offering a different antitumor spectrum, better therapeutic index and reduced toxicity than that offered by native cisplatin. Such analogues include carboplatin, ormaplatin, oxaliplatin, DWA2114R ((−)-(R)-2-aminomethylpyrrolidine (1,1-cyclobutane dicarboxylato) platinum), zeniplatin, enoplatin, lobaplatin, CI-973 (SP-4-3(R)-1,1-cyclobutane-dicarboxylato(2-)-(2-methyl-1,4-butanediamine-N,N')platinum), 254-S nedaplatin and JM-216 (bis-acetato-ammine-dichloro-cyclohexylamine-platinum(IV)) (Weiss, et al., 1993). Some cisplatin analogues, such as spiroplatin, have been found to be more toxic than native cisplatin. While more toxic analogues are not desirable for intravenous administration in free form, such analogues may have use in liposome-entrapped form, which reduces drug toxicity.

For purposes of the present invention, analogues having some degree of water solubility, such as carboplatin, iproplatin and others, are preferred so that the drug is entrapped primarily in the inner aqueous compartment of the liposome.

In a preferred embodiment, the cisplatin analogue is carboplatin, (1,1-cyclobutane-dicarboxylate-diammineplatinum), which contains organic ligands in a 4-coordinate planar complex of platinum. This cisplatin analogue demonstrated equivalent or greater antitumor activity than cisplatin and less nephrotoxicity in preclinical studies (Weiss, et al., 1993).

Liposomes containing a cisplatin analogue may be administered alone or in combination with other chemotherapeutic agents, in free form or in liposome-entrapped form, as discussed above with respect to native cisplatin.

II. Preparing the Liposome Composition

Section A below describes synthesis of vesicle-forming lipids derivatized with a hydrophilic polymer for use in forming the liposomes of the present invention. Section B describes a method of preparing liposomes including the derivatized lipids and a cisplatin compound.

A. Preparation of Derivatized Vesicle-Forming Lipids

Figure 2:
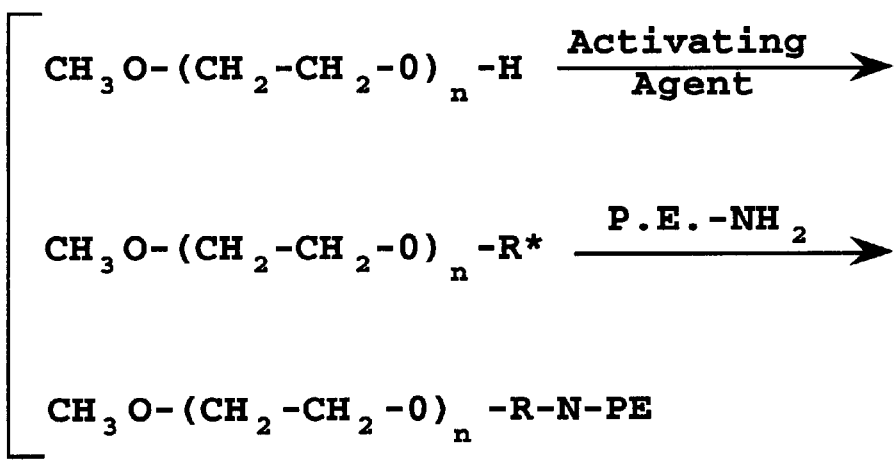
FIG. 2 illustrates a general reaction scheme for derivatizing a vesicle-forming lipid with a polyalkylether.

FIG. 2 shows a general reaction scheme for preparing a vesicle-forming lipid derivatized with a biocompatible, hydrophilic polymer, as exemplified by polyethylene glycol (PEG), which is readily water soluble, can be coupled to vesicle-forming lipids, and is tolerated in vivo without toxic effects. The polymer is preferably capped by a methoxy, ethoxy or other unreactive group at one end, or is a polymer in which one end is more reactive than the other.

The polymer is activated at one end by reaction with a suitable activating agent, such as cyanuric acid, diimadozle, anhydride reagent, or the like, as described below. The activated compound is then reacted with a vesicle-forming lipid, such as phosphatidylethanol (PE), to produce the derivatized lipid.

Alternatively, the polar group in the vesicle-forming lipid may be activated for reaction with the polymer, or the two groups may be joined in a concerted coupling reaction, according to known coupling methods. PEG capped at one end with a methoxy or ethoxy group can be obtained commercially in a variety of polymer sizes, e.g., 500–20,000 dalton molecular weights.

The vesicle-forming lipid is preferably one having two hydrocarbon chains, typically acyl chains, and a polar head group, such as those listed above.

Figure 3:
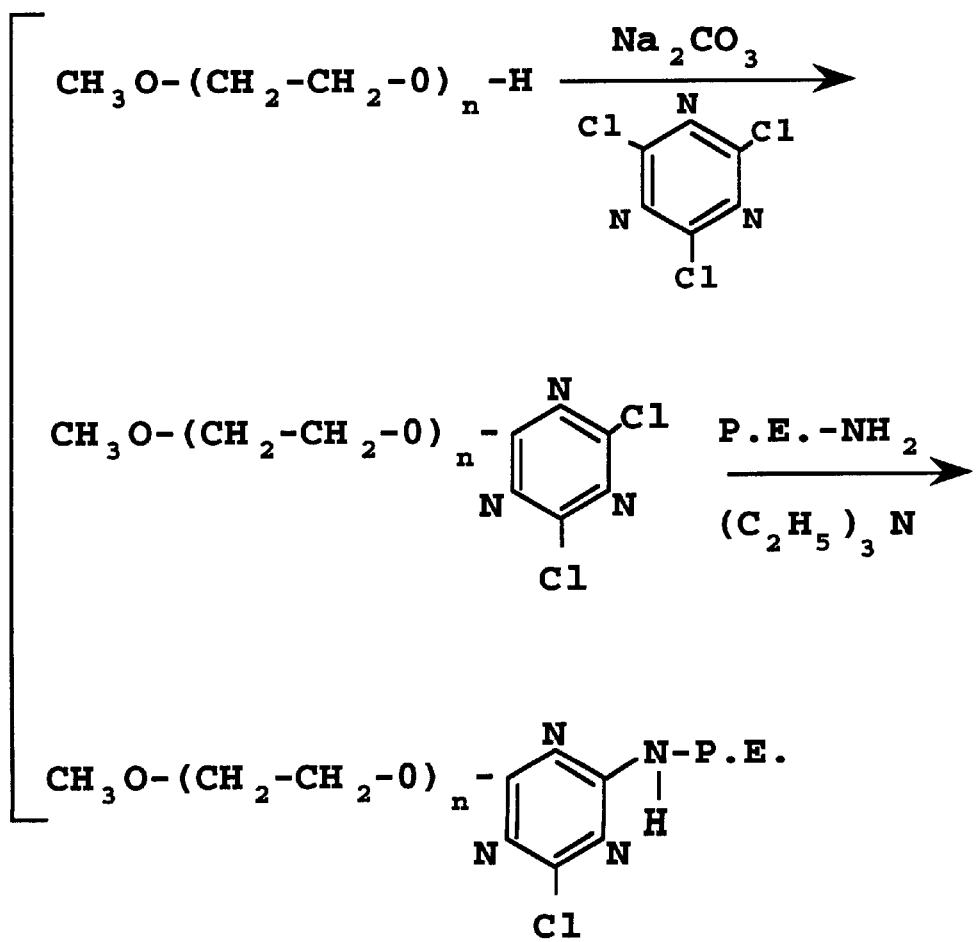
FIG. 3 is a reaction scheme for preparing phosphatidylethanolamine derivatized with polyethyleneglycol via a cyanuric chloride linking agent.

FIG. 3 shows a reaction scheme for producing a PE-PEG lipid in which the PEG is derivatized to PE through a cyanuric chloride group. Details of the reaction are provided in Example 1. Briefly, methoxy-capped PEG is activated with cyanuric chloride in the presence of sodium carbonate under conditions which produced the activated PEG compound in the figure. This material is purified to remove unreacted cyanuric acid. The activated PEG compound is reacted with PE in the presence of triethylamine to produce the desired PE-PEG compound, also shown in the figure. The yield is about 8–10% with respect to initial quantities of PEG.

The method just described may be applied to a variety of lipid amines, including PE, cholesteryl amine, and glycolipids with sugar-amine groups.

Figure 4:
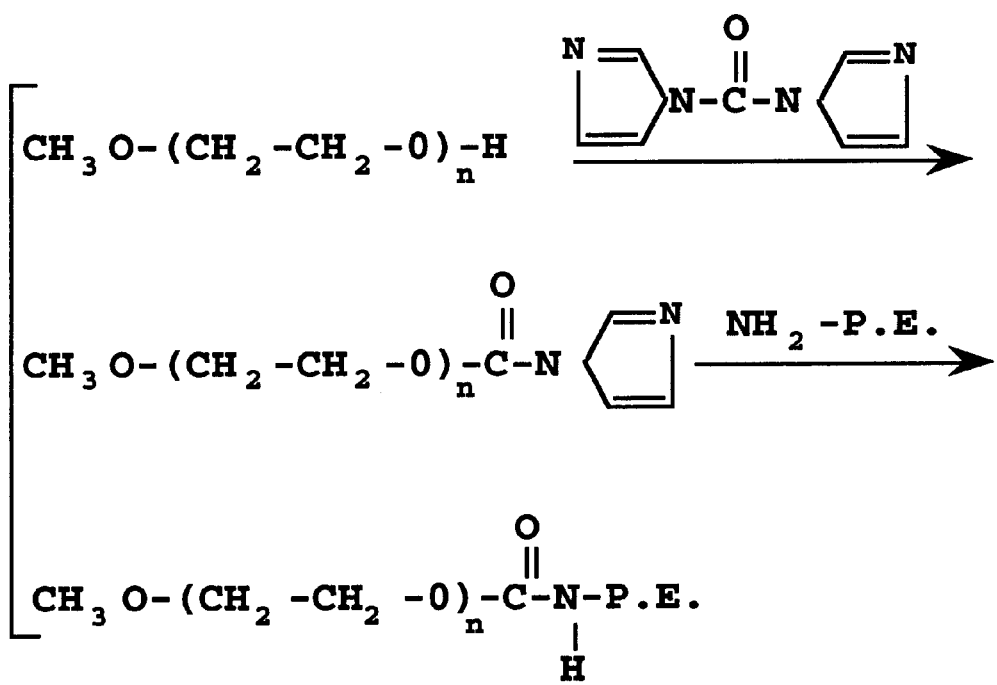
FIG. 4 illustrates a reaction scheme for preparing phosphatidylethanolamine derivatized with polyethyleneglycol by means of a diimidazole activating reagent.

A second method of coupling a polyalkylether, such as capped PEG to a lipid amine is illustrated in FIG. 4. Here the capped PEG is activated with a carbonyl diimidazole coupling reagent, to form the activated imidazole compound shown in FIG. 4. Reaction with a lipid amine, such as PE leads to PEG coupling to the lipid through an amide linkage, as illustrated in the PEG-PE compound shown in the figure. Details of the reaction are given in Example 2.

B. Liposome Preparation

The liposomes may be prepared by a variety of techniques, such as those detailed in Szoka et al, 1980. One method for preparing drug-containing liposomes is the reverse phase evaporation method, described by Szoka and in U.S. Pat. No. 4,235,871. Reverse phase evaporation vesicles (REVs) have typical average sizes between 2–4 microns and are predominantly oligolamellar, that is, contain one or a few lipid bilayer shells.

In another method, multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The liposomes are then sized, and one effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, 1990).

In the present invention, the liposome composition is typically prepared with between about 25–80 mole percent vesicle-forming lipids, 10–40 mole percent cholesterol, and 1–20 mole percent polymer-derivatized lipid. One exemplary liposome formulation includes hydrogenated soy phosphatidylcholine (HSPC) and cholesterol (Chol), in about a 1:1 molar ratio, and between about 1–5 mole % of DSPE-PEG, added to form liposomes with an inner and outer bilayer surface coating of PEG.

Generally, the cisplatin compound is incorporated into liposomes during liposome formation by adding the solution of lipids to a solution containing the drug, as will be described below.

In accordance with the method of the invention, and as described in Example 3, a lipid solution containing between 50–200 mg/ml of total lipids consisting of mPEG-DSPE, HSPC and cholesterol (molar ratio of 50.6/44.3/5.1) was prepared by dissolving the lipids in warm (60–65°) ethanol. An aqueous solution of cisplatin (8.5 mg/ml cisplatin in 0.9% sodium chloride) was warmed to a temperature sufficient to significantly increase its solubility over the compound's solubility at room temperature, specifically, the cisplatin solution was heated to about 63° C., increasing the cisplatin solubility approximately eight-fold, from 1 mg/ml to 8.5 mg/ml.

The cisplatin solution and the lipid solution were added together to form liposomes, with the temperature of the mixture maintained at between 60–65° C.

The liposomes, following diafiltration and dialysis, were extruded through 0.2 μm and 0.1 μm polycarbonate filters to size the liposomes to between about 100–120 nm. The liposome suspension was cooled to room temperature, and the unentrapped, precipitated cisplatin was removed by filtering and by diafiltration.

The final liposomes contained an internal phase of cisplatin encapsulated at a concentration of 8.5 mg/ml in 0.9% sodium chloride and an external phase of sucrose/sodium chloride solution. Prior to packaging for stability studies, described below, and/or prior to administration, the liposome suspension was brought to a cisplatin concentration of 1.05 mg/ml with a sucrose/sodium chloride/histidine solution and the pH was adjusted to 6.5.

III. Stability of the Liposome Composition

The stability of liposomes prepared as described above (Example 3) was evaluated by (i) analyzing the liposomal suspension for cisplatin and platinum concentrations, (ii) determining percent of encapsulated platinum, (iii) measuring liposome size, and (iv) measuring the pH of the liposome suspension, each as a function of time and temperature.

As described in Example 4, cisplatin concentration was measured by assaying the liposome suspension for cisplatin concentration by high pressure liquid chromatography (HPLC). In this method, an organic solvent is added to the liposome sample to disrupt the lipid bilayer, releasing the entrapped cisplatin, prior to assaying for cisplatin concentration. The platinum concentration of the liposomal suspension was determined by atomic absorption. The percentage of encapsulated platinum was measured by separating the liposomes from unencapsulated drug via size-exclusion chromatography and assaying both the liposomal and drug fractions for platinum content by atomic absorption. Liposome size was determined by dynamic light scattering.

The results are summarized in Table 1.

TABLE 1

Stability of Cisplatin-Containing Liposomes

| Temp. | Time (month) | Cisplatin Conc. (mg/ml) | Pt Conc. (mg/ml) | % Encapsulated Platinum | Liposome size (nm) | pH |
|---|---|---|---|---|---|---|
| –40° C. | 0 | 0.92 | 0.71 | 100 | 109 | 6.50 |
|  | 1 | 0.86 | 0.71 | 99 | 106 | 6.55 |
|  | 3 | 0.86 | — | — | 114 | 6.49 |
| –20° C. | 1 | 0.85 | 0.71 | 100 | 111 | 6.56 |
|  | 3 | 0.86 | — | — | 117 | 6.49 |
|  | 18 | 1.00 | 0.69 | — | 117 | 6.29 |
| 2–8° C. | 1 | 0.85 | 0.71 | 100 | 109 | 6.61 |
|  | 3 | 0.87 | 0.68 | 100 | 109 | 6.48 |
|  | 6 | 0.90 | 0.73 | 99 | 110 | 6.54 |
|  | 18 | 0.86 | 0.71 | 99 | 109 | 6.30 |
| 30° C. | 1 | 0.70 | 0.71 | 98 | 107 | 6.43 |
|  | 3 | 0.55 | 0.68 | 93 | 107 | 6.18 |
| 40° C. | 0.5 | 0.65 | 0.71 | 96 | 110 | 6.36 |
|  | 1 | 0.53 | 0.65 | 91 | 106 | 6.25 |

Liposomes stored at temperatures of –40° C. and –20° C. showed no measurable loss in the concentrations of cisplatin or platinum after storage for three months. Nor was a significant change observed in liposome size or suspension pH after the three month storage period. At –20° C. and after 18 months of storage, the cisplatin was retained in the liposomes, as evidenced by no significant loss in either the cisplatin and platinum concentration. The liposome composition was also stable when stored at 2–8° C. for 18 months. As seen in Table 1, no measurable losses in the concentrations of cisplatin or platinum were observed. At the 18 month time point, the percentage of encapsulated platinum was 99%, indicating that all but 1% of the platinum was retained in the liposomes. That the entrapped platinum is in the form of cisplatin is evident from the cisplatin concentration, which does not decrease over the 18 month storage period.

Under more aggressive storage conditions of 30° C. and 40° C., some decrease in cisplatin and platinum concentrations was observed, and the percentage of encapsulated platinum was 93% after 3 months at 30° C. and 91% after 1 month at 40° C. Little change in liposome size was observed.

The data indicates that the liposome composition of the present invention is effective to retain the cisplatin in the liposomes in its native form, thereby providing a stable liposome composition. This stability is evidenced in particular by the 18 month time point at 2–8° C., where the concentration of cisplatin remained constant and 99% of the platinum was encapsulated in the liposomes.

The liposomes of the present invention, having an inner and an outer surface coating of hydrophilic polymer chains, were compared to "conventional" liposomes, that is, liposomes lacking the inner and outer surface coating of hydrophilic polymer chains.

As described in Example 5, cisplatin-containing liposomes were prepared in accordance with the present invention from HSPC/Chol/mPEG-DSPE in a molar ratio of 50.6/44.3/5.1. A comparative liposome composition was prepared, which was identical to the liposomes of the present invention, except mPEG-DSPE was replaced with the same molar amount of distearyl phosphatidyl glycerol (DSPG), which has the same hydrocarbon tail and the same charge in the polar head group as mPEG-DSPE. The comparative liposome composition, lacking the hydrophilic polymer, did not have a surface coating of hydrophilic polymer chains on either the inner or outer lipid bilayers.

In a first study (Example 5A), the liposome compositions were incubated at 60° C. for 6 hours. After incubation, the cisplatin concentration of the liposomal suspension, the percentage of encapsulated platinum, liposome size and suspension pH were measured, according to the procedures described above. The results, summarized in Table 2, show that after the incubation period, the liposome composition of the present invention had a 24% (0.38 mg/ml to 0.29 mg/ml) decrease in cisplatin concentration, whereas the cisplatin concentration of the comparative liposomal suspension decreased by 44% (0.25 mg/ml to 0.14 mg/ml). The percentage of encapsulated platinum of the liposomes of the present invention was 96% after incubation. The comparative liposomes had a percent platinum encapsulation of 82%, indicating that 18% of the platinum-containing species had leaked from the liposomes. In an embodiment of the invention, the liposome composition is characterized by a percent of encapsulated platinum of above about 85%, more preferably 90%, when stored at 60° C. for 6 hours.

TABLE 2

Stability of PEG-Coated Liposomes and Comparative Liposomes at 60° C. for 6 Hours

| Formulation | Incubation Temperature and Time | Cisplatin Conc. (mg/ml) | % Encapsulated Platinum | Size (nm) | pH |
|---|---|---|---|---|---|
| HSPC/chol/ mPEG-DSPE | 0<br>60° C.;<br>6 hours | 0.38<br>0.29 | 100<br>96 | 116<br>117 | —<br>— |

TABLE 2-continued

Stability of PEG-Coated Liposomes and Comparative Liposomes at 60° C. for 6 Hours

| Formulation | Incubation Temperature and Time | Cisplatin Conc. (mg/ml) | % Encapsulated Platinum | Size (nm) | pH |
|---|---|---|---|---|---|
| HSPC/chol/ DSPG (comparative composition) | 0<br>60° C.;<br>6 hours | 0.25<br>0.14 | 100<br>82 | 149<br>148 | 6.53<br>6.62 |

In a second study (Example 5B), liposomes having the compositions described above for the data presented in Table 2 were incubated at 40° C. for 2 weeks, and the results are shown in Table 3. In this study, the liposomes were diluted to a cisplatin concentration of 1.0 mg/ml in a histidine/sucrose/sodium chloride diluent described in Example 3G. After the incubation period, a 29% (from 0.75 to 0.53 mg/ml) decrease in the cisplatin concentration of the suspension containing liposomes having a PEG coating was observed. The percentage of encapsulated platinum was 95%. This data indicates that a portion of the cisplatin has converted to another molecular species, such as monohydroxymonochloro cis-diamine platinum, discussed above, and that only about 5% of the platinum-containing species leaked from the liposome after incubation at 40° C. for 2 weeks.

TABLE 3

Stability of PEG-Coated Liposomes and Comparative Liposomes at 40° C. for 2 Weeks

| Formulation | Incubation Temperature and Time | Cisplatin Conc. (mg/ml) | % Encapsulated Platinum | Size (nm) | pH |
|---|---|---|---|---|---|
| HSPC/chol/ mPEG-DSPE | 0<br>40° C.;<br>2 weeks | 0.75<br>0.53 | 100<br>95 | 108<br>114 | 6.62<br>6.09 |
| HSPC/chol/ DSPG (comparative composition) | 0<br>40° C.;<br>2 weeks | 0.51<br>0 | 100<br>81 | 146<br>137 | 6.53<br>5.84 |

The comparative liposome composition, after storage at 40° C. for 2 weeks, had no measurable cisplatin remaining in the liposomes, suggesting that nearly all of the cisplatin had converted to another molecular species. 81% of the platinum-containing species was encapsulated in the liposome—in other words, 19% of the platinum-containing species had leaked from the liposomes. Clearly, liposomes prepared in accordance with the invention to have an inner and outer surface coating of hydrophilic polymer chains have a substantially greater retention of cisplatin than the comparative liposomes.

In another study, comparative liposomes were prepared as described above and stored at 2–8° C. for 2 months. The stability data for this study is summarized in Table 4 along with the data from Table 1 at the same temperature for liposomes prepared according to the invention for comparison.

TABLE 4

Stability of PEG-Coated Liposomes and Comparative Liposomes at 2–8° C. for 2 Months

| Formulation | Time (months) at 2–8° C. | Cisplatin Conc. (mg/ml) | Pt Conc. (mg/ml) | % Encapsulated Platinum | Size (nm) | pH |
| --- | --- | --- | --- | --- | --- | --- |
| HSPC/chol/ | 0 | 0.92 | 0.71 | 100 | 109 | 6.5 |
| mPEG- | 1 | 0.85 | 0.71 | 100 | 109 | 6.61 |
| DSPE | 3 | 0.87 | 0.68 | 100 | 109 | 6.48 |
|  | 6 | 0.90 | 0.73 | 99 | 110 | 6.54 |
|  | 18 | 0.86 | 0.71 | 99 | 109 | 6.30 |
| HSPC/chol/ | 0 | 0.51 | 0.44 | 100 | 146 | 6.53 |
| DSPG (comparative composition) | 2 | 0.11 | 0.42 | 98 | 143 | 6.50 |

It is clear from the data shown in Table 4 that compared to liposomes lacking an inner and outer surface coating of hydrophilic polymer chains, the liposome composition of the present invention having such a surface coating is effective to reduced the loss of cisplatin from the liposomes. In particular, the liposome composition is effective to reduce conversion of cisplatin to other molecular species, as evidenced by comparing the cisplatin concentrations and the percentage of encapsulated platinum for the two compositions.

In summary, the stability data presented in Tables 2, 3 and 4 indicate that liposomes prepared in accordance with the present invention, having an inner and outer surface coating of hydrophilic polymer chains, provide a stably entrapped, liposomal composition of cisplatin by (1) reducing the conversion of cisplatin to other molecular species, and (2) reducing the leakage of cisplatin (and other platinum-containing species) from the liposomes.

IV. In Vivo Administration

Cisplatin-containing liposomes prepared in accordance with the invention were administered to tumor-bearing mice and compared to free cisplatin and carboplatin for antitumor efficacy. As described in Example 6, mice bearing the C26 color tumor model were treated with the liposome-entrapped cisplatin composition of the present invention, with free cisplatin or with free carboplatin. Free cisplatin was administered intravenously at the maximally tolerated dose of cisplatin, 6 mg/kg once per week for 3 weeks. Free carboplatin was given at a clinically equivalent dose to cisplatin of 100 mg/kg, also administered intravenously at the same frequency. Liposome-entrapped cisplatin was administered intravenously at the same dose and frequency as free cisplatin, 6 mg/kg once a week for 3 weeks.

Figure 5:
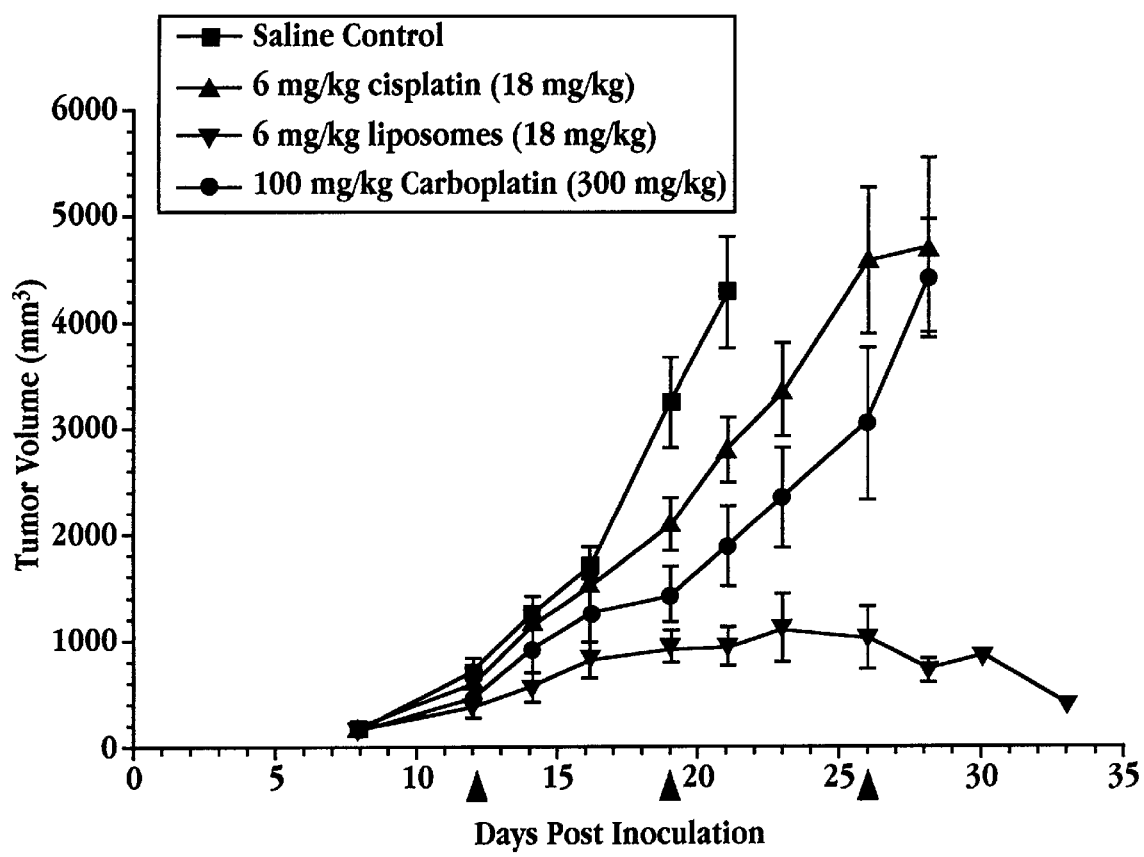
FIG. 5 is a plot of tumor volume, in mm$^3$, as a function of days post inoculation for mice inoculated with C26 colon tumor model and treated with on days 12, 19 and 26 with saline (■), free cisplatin (▲), free carboplatin (●) or with liposome-entrapped cisplatin (▼)

The results are shown in FIG. 5, where tumor volume in $mm^3$ is shown as a function of days post inoculation. Treatment of the test groups was initiated when a palpable tumor mass of about 100 $mm^3$ was evident, at about day 12. As indicated by the solid triangles along the x-axis, the test groups were treated on days 12, 19 and 26. The tumor in animals receiving saline (■) continued to grow. The animals treated with free cisplatin (▲) or with free carboplatin (●) had a similar reduction in tumor growth relative to the untreated animals. Animals treated with cisplatin entrapped in liposomes having a coating of polyethyleneglycol on the inner and outer surfaces of the liposomes (▼) had a significant reduction in tumor size relative to the animals treated with the free drug.

Figure 6:
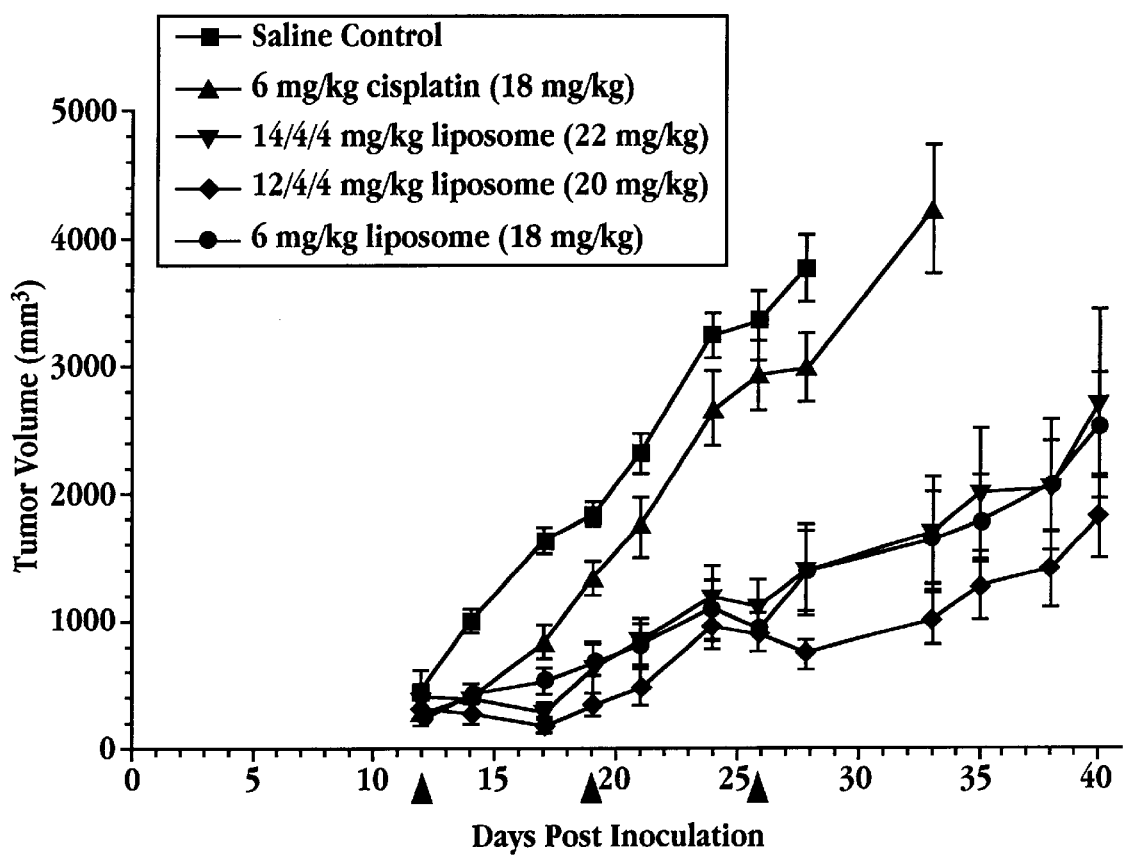
FIG. 6 is a plot of tumor volume, in mm$^3$, as a function of days post inoculation for mice inoculated with C26 colon tumor model and treated with on days 12, 19 and 26 with saline (■), free cisplatin (▲), or with liposome-entrapped cisplatin according to three dosing regimens (▼, ♦, ●)

Another study was conducted according to Example 6, where the liposome-entrapped cisplatin was administered according to different dosing schedules. That is, liposome-entrapped cisplatin was administered with a larger loading dose followed by smaller doses at the second and third weeks. The results are shown in FIG. 6, where test animals receiving saline (■) and free cisplatin (▲) at 6 mg/kg once a week for 3 weeks showed continual increase in tumor mass. The animals treated with liposome-entrapped cisplatin had significantly reduced tumor masses compared to the animals treated with saline or free cisplatin. Antitumor efficacy of the liposome-entrapped cisplatin was similar for dosing schedules of 6 mg/kg once a week for 3 weeks (●), an initial dose of 12 mg/kg with subsequent doses of 4 mg/kg on days 19 and 26 (♦) and an initial dose of 14 mg/kg with subsequent doses of 4 mg/kg on days 19 and 26 (▼).

Mice bearing the Lewis lung carcinoma tumor model were treated with cisplatin, administered intravenously and intraperitoneally, or with liposome-entrapped cisplatin, administered similarly. As described in Example 6, treatment was initiated when a tumor mass of about 100 $mm^3$ was observed in the test animals, with treatment occurring on days 7, 14 and 21 after inoculation. A control group of tumor-bearing mice were treated with saline.

Figure 7:
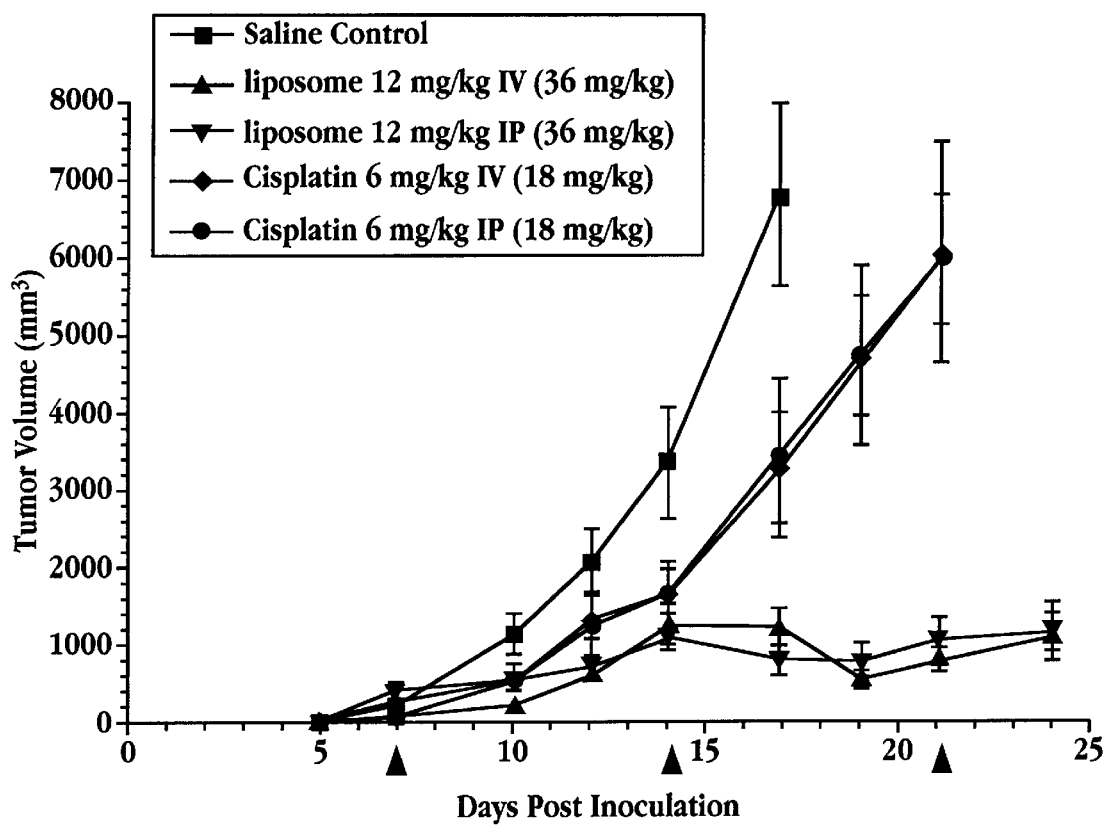
FIG. 7 is a plot of tumor volume, in mm$^3$, as a function of days post inoculation for mice inoculated with Lewis lung carcinoma and treated with on days 7, 14 and 21, with saline (■), free cisplatin IV (♦), free cisplatin IP (●) or with liposome-entrapped cisplatin IV (▲) or IP (▼)

The results are shown in FIG. 7, where tumor volume, in $mm^3$, is plotted as a function of days post inoculation. Treatment is indicated by the solid triangles along the x-axis on days 7, 14 and 21. The tumor in mice treated with saline (■) grew continually through the test period. The response in tumor mass to free cisplatin administered intravenously (♦) or intraperitoneally (●) at a dose of 6 mg/kg on the indicated treatment days was similar. Treatment with 12 mg/kg liposome-entrapped cisplatin, administered intravenously (▲) or intraperitoneally (▼) on the indicated treatment days had improved antitumor efficacy relative to the animals treated with free cisplatin. Administration intravenously and intraperitoneally were equally effective.

From the foregoing, it can be appreciated how various features and objects of the invention are met. The liposome composition of the present invention includes liposomes having an inner surface coating and an outer surface coating of hydrophilic polymer chains and an entrapped cisplatin compound. The studies performed in support of the invention demonstrate that the cisplatin is stably entrapped in the liposomes, as evidenced by retention of cisplatin and platinum after incubation for various times at several temperatures. Cisplatin stably entrapped in liposomes offers the advantages of reduced toxicity and of improved efficacy, relative to the drug administered in free form, since after administration the drug remains entrapped in the liposome with little leakage to the bloodstream. The outer surface coating of PEG chains provide a long blood circulation lifetime allowing the liposomes to reach a target site, such as a tumor.

V. Examples

The following examples are intended to illustrate, but not limit, the scope of the invention.

Materials: Cisplatin was obtained from W. C. Heraeus GmbH (Hanau, Germany). DSPE was purchased from Avanti Polar Lipids (Birmingham, Ala.) and methoxy-polyethyleneglycol (mPEG), MW 2000 dalton, was obtained from Fluka Chemie AG (Buchs, Switzerland). Cholesterol was obtained from Croda, Inc., (NY, N.Y.). HSPC was made by Lipoid K. G. (Ludwigshafen, Germany) and mPEG-DSPE was made by Sygena, Inc., (Liestal, Switzerland).

Example 1

Preparation of PEG-Derivatized DSPE linked by Cyanuric Chloride

A. Preparation of Activated PEG 2-0-Methoxypolyethylene glycol 1900-4,6-dichloro-1,3,5 triazine previously called activated PEG was prepared as described in *J. Biol. Chem.* 252:3582 (1977) with the following modifications.

Cyanuric chloride (5.5 g; 0.03 mol) was dissolved in 400 ml of anhydrous benzene containing 10 g of anhydrous sodium carbonate, and PEG-1900 (19 g; 0.01 mol) was added and the mixture was stirred overnight at room temperature. The solution was filtered, and 600 ml of petroleum ether (boiling range, 35–60°) was added slowly with stirring. The finely divided precipitate was collected on a filter and redissolved in 400 ml of benzene. The precipitation and filtration process was repeated several times until the petroleum ether was free of residual cyanuric chloride as determined by high pressure liquid chromatography on a column (250×3.2 mm) of 5-m "LiChrosorb" (E. Merck), developed with hexane, and detected with an ultraviolet detector. Titration of activated PEG-1900 with silver nitrate after overnight hydrolysis in aqueous buffer at pH 10.0, room temperature, gave a value of 1.7 mol of chloride liberated/mol of PEG.

TLC analysis of the product was effected with TLC reversed-phase plates obtained from Baker using methanol:water, 4:1 (v/v) as developer and exposure to iodine vapor for visualization. Under these conditions, the starting methoxy polyglycol 1900 appeared at $R_f$=0.54 to 0.60. The activated PEG appeared at $R_f$=0.41. Unreacted cyanuric chloride appeared at $R_f$=0.88 and was removed.

The activated PEG was analyzed for nitrogen and an appropriate correction was applied in selecting the quantity of reactant to use in further synthetic steps. Thus, when the product contained only 20% of the theoretical amount of nitrogen, the quantity of material used in the next synthetic step was increased by 100/20, or 5-fold. When the product contained 50% of the theoretical amount of nitrogen, only 100/50 or a 2-fold increase was needed.

B. Preparation of N-(4-Chloro-polyglycol 1900)-1,3,5-Triazinyl Egg Phosphatidylethanolamine In a screw-capped test tube, 0.74 ml of a 100 mg/ml (0.100 mmole) stock solution of egg phosphatidylethanolamine in chloroform was evaporated to dryness under a stream of nitrogen and was added to the residue of the activated PEG described in section A, in the amount to provide 205 mg (0.100 mmole). To this mixture, 5 ml anhydrous dimethyl formamide was added. 27 microliters (0.200 mmole) triethylamine was added to the mixture, and the air was displaced with nitrogen gas. The mixture was heated overnight in a sand bath maintained at 110° C.

The mixture was then evaporated to dryness under vacuum and a pasty mass of crystalline solid was obtained. This solid was dissolved in 5 ml of a mixture of 4 volumes of acetone and 1 volume of acetic acid. The resulting mixture was placed at the top of a 21 mm×240 mm chromatographic absorption column packed with silica gel (Merck Kieselgel 60, 70–230 mesh) which had first been moistened with a solvent composed of acetone acetic acid, 80/20; v/v.

The column chromatography was developed with the same solvent mixture, and separate 20 to 50 ml aliquots of eluent were collected. Each portion of eluent was assayed by TLC on silica gel coated plates, using 2-butanone/acetic acid/water; 40/25/5; v/v/v as developer and iodine vapor exposure for visualization. Fractions containing only material of $R_f$=about 0.79 were combined and evaporated to dryness under vacuum. Drying to constant weight under high vacuum afforded 86 mg (31.2 micromoles) of nearly colorless solid N-(4-chloro-polyglycol 1900)-1,3,5-triazinyl egg phosphatidylethanolamine containing phosphorous.

The solid compound was taken up in 24 ml of ethanol/chloroform; 50/50 and centrifuged to remove insoluble material. Evaporation of the clarified solution to dryness under vacuum afforded 21 mg (7.62 micromoles) of colorless solid.

Example 2

Preparation of PEG-Derivatized DSPE linked by Carbamate

A. Preparation of the Imidazole Carbamate of Polyethylene Glycol Methyl Ether 1900

9.5 grams (5 mmoles) of polyethylene glycol methyl ether 1900 obtained from Aldrich Chemical Co. was dissolved in 45 ml benzene which had been dried over molecular sieves. 0.89 grams (5.5 mmoles) of pure carbonyl diimidazole was added. The purity was checked by an infra-red spectrum. The air in the reaction vessel was displaced with nitrogen. Vessel was enclosed and heated in a sand bath at 75° C. for 16 hours.

The reaction mixture was cooled and a clear solution formed at room temperature. The solution was diluted to 50.0 ml with dry benzene and stored in the refrigerator as a 100 micromole/ml stock solution of the imidazole carbamate of PEG ether 1900.

B. Preparation of the Phosphatidylethanolamine Carbamate of Polyethylene Glycol Methyl Ether 1900

10.0 ml (1 mmol) of the 100 mmol/ml stock solution of the imidazole carbamate of polyethylene glycol methyl ether 1900 (compound X) was pipetted into a 10 ml pear-shaped flask. The solvent was removed under vacuum. 3.7 ml of a 100 mg/ml solution of egg phosphatidyl ethanolamine (V) in chloroform (0.5 mmol) was added. The solvent was evaporated under vacuum. 2 ml of 1,1,2,2-tetrachloroethylene and 139 microliters (1.0 mmol) of triethylamine VI was added. The vessel was closed and heated in a sand bath maintained at 95° C. for 6 hours. At this time, thin-layer chromatography was performed with fractions of the above mixture to determine the extent of conjugation on SiO2 coated TLC plates, using butanone/acetic acid/water; 40/5/5; v/v/v; as developer. Iodine vapor visualization revealed that most of the free phosphatidylethanolamine of Rf=0.68, had reacted, and was replaced by a phosphorous-containing lipid at $R_f$=0.78 to 0.80.

The solvent from the remaining reaction mixture was evaporated under vacuum. The residue was taken up in 10 ml methylene chloride and placed at the top of a 21 mm×270 mm chromatographic absorption column packed with Merck Kieselgel 60 (70–230 mesh silica gel), which has been first rinsed with methylene chloride. The mixture was passed through the column, in sequence, using the following solvents.

| ml | Volume % of Methylene Chloride | Volume % Methanol with 2 Acetic Acid |
| --- | --- | --- |
| 100 | 100% | 0% |
| 200 | 95% | 5% |
| 200 | 90% | 10% |
| 200 | 85% | 15% |
| 200 | 60% | 40% |

50 ml portions of eluent were collected and each portion was assayed by TLC on Si02—coated plates, using $I_2$ vapor absorption for visualization after development with chloroform/methanol/water/concentrated ammonium hydroxide; 130/70/8/0.5%; v/v/v/v. Most of the phosphates were found in fractions 11, 12, 13 and 14.

These fractions were combined, evaporated to dryness under vacuum and dried in high vacuum to constant weight. They yielded 669 mg of a colorless wax of phosphatidyl ethanolamine carbamate of polyethylene glycol methyl ether. This represented 263 micromoles and a yield of 52.6% based on the phosphatidylethanolamine.

An NMR spectrum of the product dissolved in deuterochloroform showed peaks corresponding to the spectrum for egg PE, together with a strong singlet due to the methylene groups of the ethylene oxide chain at Delta=3.4 ppm. The ratio of methylene protons from the ethylene oxide to the terminal methyl protons of the PE acyl groups was large enough to confirm a molecular weight of about 2000 for the polyethylene oxide portion of the molecule of the desired product polyethylene glycol conjugated phosphatidylethanolamine carbamate, M.W. 2,654.

Example 3

Liposome Preparation

A. Step 1: Drug Solution Preparation

Sterile water was heated to 63–67° C. in a TEFLON-lined pressure vessel and sodium chloride (0.9%) was added. Cisplatin was added at a concentration of 8.5 mg/ml and mixed until dissolved, approximately 15–25 minutes.

B. Step 2: Lipid Dissolution 257.0 g PEG-DSPE, 719.4 g HSPC and 308.4 g cholesterol (molar ratio of 50.6/44.3/5.1) were added to 900 ml dehydrated ethanol at 60–65° C. and mixed until dissolved, approximately 2 hours. The dissolved lipids were added to 7670 g of drug solution to give a total lipid concentration of approximately 150 mg/ml.

C. Step 3: Lipid Hydration/Drug Loading

The warm lipid solution was rapidly added to the warm (63–67° C.) drug solution, with mixing, to form a suspension of liposomes having heterogeneous sizes. The suspension was mixed for one hour at 63–67° C. The cisplatin concentration in the hydration mixture was 7.2 mg/ml and, at this stage, approximately 30% of the drug was encapsulated in the liposomes. 10% of the total solution volume was ethanol and the total lipid concentration was 150 mg lipid/ml.

D. Step 4: Extrusion

The liposomes were sized to the desired mean particle diameter by controlled extrusion through polycarbonate filter cartridges housed in Teflon-lined stainless steel vessels. The liposome suspension was maintained at 63–65° C. throughout the extrusion process, a period of 6–8 hours.

E. Step 5: Low-Grade Filtering

After sizing, the liposome suspension was cooled to room temperature (20–25° C.) and filtered through a 1.2 $\mu$m 142-mm Gelman Versapor filter (acrylic copolymer on a Nylon 66 support) to remove precipitated drug. At this stage approximately 50% of the drug was encapsulated.

F. Step 6: Diafiltration

A sucrose/sodium chloride solution was prepared by dissolving sucrose (100 mg/ml) and sodium chloride (0.058 mg/ml) in sterile water. The pH of the solution was adjusted to approximately 5.5 with 2 N HCl or NaOH. The solution was filtered through a 0.22 $\mu$m Durapore filter.

The liposome suspension was diluted in approximately a 1:1 (v/v) ratio with the sucrose/sodium chloride solution and diafiltered through a polysulfone hollow-fiber ultrafilter. Eight volume exchanges were performed against the sucrose/sodium chloride solution to remove the ethanol and unencapsulated drug. The process fluid temperature was maintained at about 20–30° C. Total diafiltration time was approximately 4.5 hours.

The liposome suspension was then concentrated to approximately 1.2 mg cisplatin/ml by ultrafiltration. The post diafiltration process fluid was analyzed for cisplatin content by HPLC. The liposomes had an internal phase of 8.5 mg/ml cisplatin in 0.9% sodium chloride and an external phase of sucrose/sodium chloride solution.

G. Step 7: Dilution

A diluent was prepared by dissolving histidine (10 mM) in a sucrose/sodium chloride (10 sucrose/1 mM NaCl) solution to a target histidine concentration of 1.55 mg/ml in the final mixture. The liposome suspension was diluted to a target cisplatin concentration of 1.05 mg/ml with the histidine diluent. The pH of the suspension was adjusted to 6.5 with 2N NaOH or HCl.

H. Step 8: Sterile Filtration

The liposome suspension was heated to 33–38° C. and filtered through a 0.2 $\mu$m Gelman Super polyethersulfone filter. Total filtration time was approximately 10 minutes.

Example 4

Stability of Cisplatin Liposomes

A suspension of cisplatin-containing liposomes was prepared as described in Example 3. 5 ml aliquots of the liposome suspension were placed in 10 cc glass vials, sealed under aseptic conditions, and placed in incubators or refrigerators at the following temperatures: −40° C., −20° C., 2–8° C., 30° C., 40° C. At intervals, samples from each vial stored at each temperature were drawn and tested in triplicate for:

1. Cisplatin concentration: The concentration of cisplatin was measured by disrupting the liposome bilayer with an organic solvent to release the entrapped cisplatin and then determining the cisplatin concentration by high pressure liquid chromatography (HPLC);
2. Platinum concentration, measured by atomic absorption;
3. Percent of encapsulated platinum: The percent encapsulated platinum was determined by separating the liposomes from unencapsulated cisplatin by size-exclusion chromatography and assaying the liposomal and drug fractions for platinum content by atomic absorption;

4. Liposome size, determined by dynamic light scattering; and
5. pH of liposome suspension.
The results are shown in Table 1.

Example 5

Comparative Stability Studies

Cisplatin-containing liposomes were prepared with no inner and outer surface coating of hydrophilic polymer chains for comparison to the liposomes of the present invention. Comparative liposomes were prepared as described in Example 3, except distearyl phosphatidylglycerol (DSPG) was substituted for the PEG-DSPE derivative, e.g., the liposome composition consisted of HSPC/Chol/DSPG in a molar ratio of 50.6/44.3/5.1.

A. Incubation at 60° C. for 6 Hours

Stability of the comparative liposome composition and the liposome composition of the present invention were compared by diluting the liposome samples with saline (1:1 v:v) and incubating the suspensions for 6 hours at 60° C. After incubation, the samples were tested for cisplatin concentration, % platinum encapsulation, liposome size and pH, according to the procedures described in Example 4. The results are summarized in Table 2.

B. Incubation at 40° C. for 2 Weeks

The liposome compositions were diluted to a cisplatin concentration of 1 mg/ml with the histidine/sucrose/sodium chloride diluent described in Example 3G. The liposome suspensions were incubated at 40° C. for 2 weeks, after which the cisplatin concentration, % platinum encapsulation, liposome size and pH were measured. The results are summarized in Table 3.

Example 6

Treatment of Tumor-Bearing Mice

Liposomes containing entrapped cisplatin were prepared as described in Example 3 and were composed of HSPC, cholesterol and mPEG-DSPE in a 50.6/44.3/5/1 molar ratio. The total lipid content was approximately 71 mg/ml and the cisplatin concentration was 1 mg/ml.

A. C26 Colon Tumor Model

The C26 colon tumor model was grown in Balb/c, male mice (Simonson Laboratories, Inc., Gilroy, Calif.). Tumors were harvested from donor mice for and minced finely in RPMI media with 10% fetal calf serum (FCS). Tumors were then digested with enzyme mix (10 ml 0.25% protease type IX and 0.25% collagenase type IV in Hank's balanced salt solution (HBSS) and 0.2% ml 0.02% DNase in HBSS) for 30–60 minutes at 37° C. Single cell suspension of tumor cells was washed twice in RPMI media with FCS, concentrated by centrifugation and resuspended in RPMI media with FCS for inoculation. One million tumor cells (0.1 ml) were inoculated in the left flank of 5–6 week old mice.

Throughout all experiments, animals were maintained in 12 hour light:12 hour dark cycles, fed ad libitum rodent chow and water.

1. Comparison of Free Drug and Liposome-entrapped Drug. The tumor-bearing mice were divided into groups of n=9 for treatment with liposome-entrapped cisplatin, free cisplatin (Platinol-AQ®, Bristol Laboratories, Princeton, N.J.) or free carboplatin (Paraplatin®, Bristol Laboratories) according to the treatment regimen shown in Table 5.

TABLE 5

| Test Compound | IV Dose | Cumulative Dose | Frequency |
| --- | --- | --- | --- |
| Saline | 0.1 ml | | once/week × 3 |
| Cisplatin | 6 mg/kg | 18 mg | once/week × 3 |
| Carboplatin | 100 mg/kg | 300 mg | once/week × 3 |
| Liposomal Cisplatin | 6 mg/kg | 18 mg | once/week × 3 |

Free cisplatin and liposome-entrapped cisplatin were administered intravenously at a dose of 6 mg/kg weekly for 3 weeks. Carboplatin was administered intravenously at a dose of 100 mg/kg weekly for 3 weeks. The control group of mice (n=5) received 0.1 ml of saline intravenously weekly for 3 weeks. The results are shown in FIG. 5.

2. Altered Dosing Schedule. Mice were inoculated with the C26 colon tumor cells according to the above-described procedure. Treatment of the tumor-bearing mice was initiated when the majority of animals had palpable tumors mass of about 100 $mm^3$. The mice were treated with liposome-entrapped cisplatin or with free cisplatin once per week for 3 weeks according to the regimen shown in Table 6.

TABLE 6

| Test Compound | IV Dose | Cumulative Dose | Frequency |
| --- | --- | --- | --- |
| Saline | 0.1 ml | — | once/week × 3 |
| Cisplatin | 6 mg/kg | 18 mg/kg | once/week × 3 |
| Liposomal Cisplatin | 14/4/4 mg/kg[1] | 22 mg/kg | once/week × 3 |
| Liposomal Cisplatin | 12/4/4 mg/kg[1] | 20 mg/kg | once/week × 3 |
| Liposomal Cisplatin | 6 mg/kg | 18 mg/kg | once/week × 3 |

[1]Initial loading dose followed by 2 smaller doses.

Free cisplatin was administered intravenously at a dose of 6 mg/kg once per week for 3 weeks to tumor-bearing mice (n=9). Cisplatin entrapped in liposomes, prepared as described above, was administered intravenously according to three dosing schedules to tumor-bearing mice. One group (n=9) received 6 mg/kg liposome-entrapped cisplatin once per week for 3 weeks; another group (n=9) received a first dose of 14 mg/kg, followed by subsequent doses in weeks 2 and 3 of 4 mg/kg; another group (n=9) received a first dose of 12 mg/kg, followed by 4 mg/kg in weeks 2 and 3 of the study. The control group (n=5) received saline on each treatment day. The results are shown in FIG. 6.

B. Mice Bearing Lewis Lung Tumor Model

The Lewis lung tumor (LL/2, CRL-1642, ATCC, Rockville, Md.) model was grown in G6C3-F1, male mice (Simonson Laboratories, Inc., Gilroy, Calif.). Tumors were harvested from donor mice and processed as above for inoculation of an experiment. One million tumor cells (0.1 ml) were inoculated in the left flank of 5–6 week old, male, B6C3-F1 mice.

Treatment of the tumor-bearing animals was initiated seven days after inoculation, when the majority of animals had palpable tumor masses. Animals were treated according to the regimen shown in Table 7.

TABLE 7

| Test Compound | Dose (Route) | Cumulative Dose | Frequency |
| --- | --- | --- | --- |
| Saline | 0.1 ml (IV) | — | once/week × 3 |
| Cisplatin | 6 mg/kg (IV) | 18 mg/kg | once/week × 3 |

TABLE 7-continued

| Test Compound | Dose (Route) | Cumulative Dose | Frequency |
| --- | --- | --- | --- |
| Cisplatin | 6 mg/kg (IP) | 18 mg/kg | once/week × 3 |
| Liposomal Cisplatin | 12 mg/kg (IV) | 36 mg/kg | once/week × 3 |
| Liposomal Cisplatin | 12 mg/kg (IP) | 36 mg/kg | once/week × 3 |

The control group (n=9) received saline on the treatment days (days 7, 14 and 21). Two groups of animals received free cisplatin at 6 mg/kg on each treatment day; in one group (n=9) the free cisplatin administered intravenously, in the other group (n=9), the drug administered intraperitoneally. Two groups received liposome-entrapped cisplatin at 12 mg/kg on each treatment day; one group (n=7) receiving the dose intravenously, the other group (n=9) receiving the dose intraperitoneally. The results are shown in FIG. 7.

Although the invention has been described with respect to particular embodiments, it will be apparent to those skilled in the art that various changes and modifications can be made without departing from the invention.

It is claimed:

1. A liposomal composition containing an entrapped cisplatin compound, comprising liposomes having an outer surface and an inner surface defining an aqueous liposome compartment, and being composed of a vesicle-forming lipid and between about 1–20 mole percent of a vesicle-forming lipid derivatized with a hydrophilic polymer having an uncharged end cap, said liposomes being formed such that the hydrophilic polymer forms a coating of hydrophilic polymer chains on both said inner and outer surfaces, and the cisplatin compound entrapped in said liposomes, said compound remaining entrapped in the liposomes in its native form with substantially greater retention when compared to liposomes lacking said polymer coating.

2. The composition of claim 1, wherein said hydrophilic polymer chains are composed of a hydrophilic polymer selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide.

3. The composition of claim 2, wherein said hydrophilic polymer chains are composed of polyethylene glycol.

4. The composition of claim 1, wherein said liposomes have sizes of between about 80–160 nm.

5. The composition of claim 1, wherein said vesicle forming lipid is hydrogenated soy phosphatidylcholine and said derivatized vesicle forming lipid is distearyl phosphatidylethanolamine derivatized with polyethylene glycol.

6. The composition of claim 1, wherein said cisplatin compound is cisplatin or a cisplatin analogue selected from the group consisting of carboplatin, ormaplatin, oxaliplatin, ((−)-(R)-2-aminomethylpyrrolidine (1,1-cyclobutane dicarboxylato))platinum, zeniplatin, enloplatin, lobaplatin, (SP-4-3(R)-1,1-cyclobutane-dicarboxylato(2-)-(2-methyl-1,4-butanediamine-N,N'))platinum, nedaplatin and bis-acetato-ammine-dichloro-cyclohexylamine-platinum(IV).

7. The composition of claim 6, wherein said cisplatin compound is cisplatin.

8. The composition of claim 7, wherein said cisplatin compound is entrapped at a drug-to-lipid ratio of between about 10 to 20 μg/mg total lipid.

9. The composition of claim 1, wherein said liposomes are suspended in an aqueous medium at a liposome lipid concentration between 50–200 mg/ml, and the composition is characterized by a percent of encapsulated platinum of above about 90% when stored at 60° C. for a 6 hour period.

10. A method of entrapping a cisplatin compound in liposomes, comprising heating an aqueous solution of a cisplatin compound to a temperature sufficient to increase its solubility at least two-fold over the compound's solubility at room temperature;

adding to the heated solution a vesicle-forming lipid and between about 1–20 mole percent of a vesicle-forming lipid derivatized with a hydrophilic polymer having an uncharged end cap; and by said adding, forming liposomes having an inner surface coating and an outer surface coating of said hydrophilic polymer and said cisplatin compound remaining entrapped in the liposomes in its native form with substantially greater retention than in liposomes lacking said inner and outer surface coating.

11. The method of claim 10, wherein said heating includes heating native cisplatin to a temperature sufficient to achieve a two-fold increase in cisplatin solubility over its room temperature solubility.

12. The method of claim 11, wherein said adding includes adding a solution of vesicle-forming lipids heated to within about 10° C. of the temperature of the cisplatin solution.

13. The method of claim 11, wherein said adding includes adding a solution containing a vesicle-forming lipid having a phase transition temperature within about 10° C. of the temperature to which the solution containing the cisplatin compound is heated.

14. The method of claim 10, wherein said adding includes adding a solution containing a vesicle-forming lipid having a phase transition temperature between 40–70° C.

* * * * *